United States Patent [19]

Kurtz et al.

[11] 4,051,193

[45] Sept. 27, 1977

[54] PROCESS FOR PRODUCING ETHYLENE FROM ETHANE

[75] Inventors: Bruce E. Kurtz, Marcellus; Edmund W. Smalley, Brewerton, both of N.Y.

[73] Assignee: Allied Chemical Corporation, Morris Township, N.J.

[21] Appl. No.: 622,326

[22] Filed: Oct. 14, 1975

[51] Int. Cl.² .......................... C07C 5/42; C07C 5/44; C07C 5/48
[52] U.S. Cl. .................. 260/683.3; 208/129; 260/662 A; 260/683 R
[58] Field of Search ............ 260/683 R, 683.3, 662 A, 260/677 XA (U.S. only); 208/129, 115; 23/277

[56] References Cited
U.S. PATENT DOCUMENTS

| | | | |
|---|---|---|---|
| 2,397,638 | 4/1946 | Bell et al. | 260/683 |
| 2,423,493 | 7/1947 | Folkins | 260/683 |
| 3,213,015 | 10/1965 | Atkinson et al. | 208/129 |
| 3,336,412 | 8/1967 | Lyon et al. | 260/683.3 |
| 3,541,179 | 11/1970 | Okagami et al. | 260/683.3 |
| 3,558,735 | 1/1971 | Beard | 260/683.3 |
| 3,987,119 | 10/1976 | Kurtz et al. | 260/683.3 X |

Primary Examiner—Delbert E. Gantz
Assistant Examiner—C. E. Spresser
Attorney, Agent, or Firm—Gerhard H. Fuchs; Jack B. Murray, Jr.

[57] ABSTRACT

Process and apparatus are provided for producing ethylene by the oxidative dehydrogenation of ethane wherein ethane is introduced to a cylindrical jet reactor wherein the ethane is reacted at elevated temperatures with a gas mixture containing oxygen and chlorine, introduced to the reactor through a jet positioned substantially coaxial to the longitudinal axis of the reactor.

10 Claims, 1 Drawing Figure

PROCESS FOR PRODUCING ETHYLENE FROM ETHANE

BACKGROUND OF THE INVENTION

1. Field of the Invention

This invention relates to process and apparatus for producing ethylene from ethane, and more particularly to the production of ethylene by the oxidative dehydrogenation of ethane.

2. Description of the Prior Art

Processes have been developed for producing ethylene from ethane wherein ethane, oxygen and either elemental chlorine or a chlorine-containing reactant (e.g. HCl) are passed in contact with a catalyst at elevated temperatures for autothermic cracking (i.e., oxidative dehydrogenation) of ethane. See, e.g., U.S. Pat. Nos. 3,217,064; 3,278,627; 3,278,629; 3,278,630; 3,278,631; 3,308,183; 3,308,197; 3,658,933; 3,658,934; 3,702,311; and 3,862,996. The reaction of chlorine, oxygen and ethane to form ethylene, hydrogen chloride and water may be illustrated by the following equation:

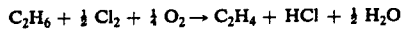

$$C_2H_6 + \tfrac{1}{2} Cl_2 + \tfrac{1}{4} O_2 \rightarrow C_2H_4 + HCl + \tfrac{1}{2} H_2O$$

While such processes produced ethylene, the conversions are typically low, requiring recycle of large amounts of unreacted ethane, thereby leading to increased equipment costs and processing expenses. In addition, use of catalyst entails added expense due to the cost of the catalyst and to the need to periodically replace catalyst which has become poisoned or otherwise inactivated as a result of impurities present in the feed streams or from various by-products formed in the reaction. While processes such as that disclosed in U.S. Pat. No. 3,336,412 have been developed which do not employ catalyst, the pyrolysis product generally contains a substantial quantity of acetylene, thereby complicating downstream recovery of the ethylene that is produced.

While generally less than about 1 weight percent of ethane fed to the reactor is converted to carbon, and thus while carbon formation does not seriously reduce the yield of ethylene, carbon depositions are disadvantageous due to the plugging of the reactor and downstream recovery equipment. While we do not wish to be limited by the theory given below, we believe that the carbon formation results from polymerization of acetylene which is in turn formed by the cracking of ethylene. The acetylene polymerization leads to formation of straight chains of increasing length whose condensation will ultimately form conjugated ring structures. Successive conjugations to form larger and larger conjugated ring structures at nucleation sites will ultimately lead to turbostratic carbon with platelets adhering to and aligned with the walls of reactor and exit lines. Continued growth of the straight chain acetylene polymers and homogenous dehydrogenation is believed to lead to amorphous carbon which is entrained in exit gases.

Thus, a process is desired which will provide ethylene from ethane while decreasing the amount of carbon deposit on process equipment.

Belgium Pat. No. 821,397, filed Oct. 23, 1974, discloses a process for preparation of ethylene dichloride and vinyl chloride from ethylene wherein the ethylene is produced by the autothermic cracking of ethane.

SUMMARY OF THE INVENTION

According to the present invention, a process is provided for the production of ethylene by the oxidative dehydrogenation of ethane which comprises introducing a gas mixture containing oxygen and chlorine under pressure to an elongated reaction zone as a gas feed stream; introducing a gas containing ethane to said reaction zone about said gas feed stream; maintaining said reaction zone under conditions sufficient to effect reaction of oxygen, chlorine and ethane in said zone to form ethylene; and withdrawing product reaction mixture containing ethylene from said reaction zone.

The process of the present invention provides reaction between the chlorine, oxygen and ethane in the longitudinal reaction zone as the ethane flows longitudinally through the reaction zone co-current with the gas mixture containing the oxygen and chlorine. The present invention has been found to result in ethylene yields per pass of up to 70 percent and more.

Apparatus for carrying out the process of the present invention are also provided and comprise an elongated housing having an elongated reaction zone internally disposed therein; first gas inlet means for introducing a gas mixture containing oxygen and chlorine into said reaction zone as a gas feed stream, substantially along the longitudinal axis of said zone; second gas inlet means for introducing gas containing ethane into said reaction zone about the longitudinal axis of said zone and co-current to the flow of said gas mixture through said reaction zone; means for maintaining said reaction zone under conditions sufficient to effect reaction therein of oxygen, chlorine and ethane to form ethylene; and means for withdrawing reaction product containing ethylene from said reaction zone.

The present invention advantageously provides production of ethane at high conversions with excellent yields, while suppressing the formation of various by-products such as carbon monoxide and methane and providing decreased quantities of carbon formation on processing equipment and downstream recovery apparatus.

BRIEF DESCRIPTION OF THE DRAWING

The accompanying drawing is a longitudinal half section of one embodiment of an axial jet reactor of the present invention.

DETAILED DESCRIPTION OF THE INVENTION

Figure 1:
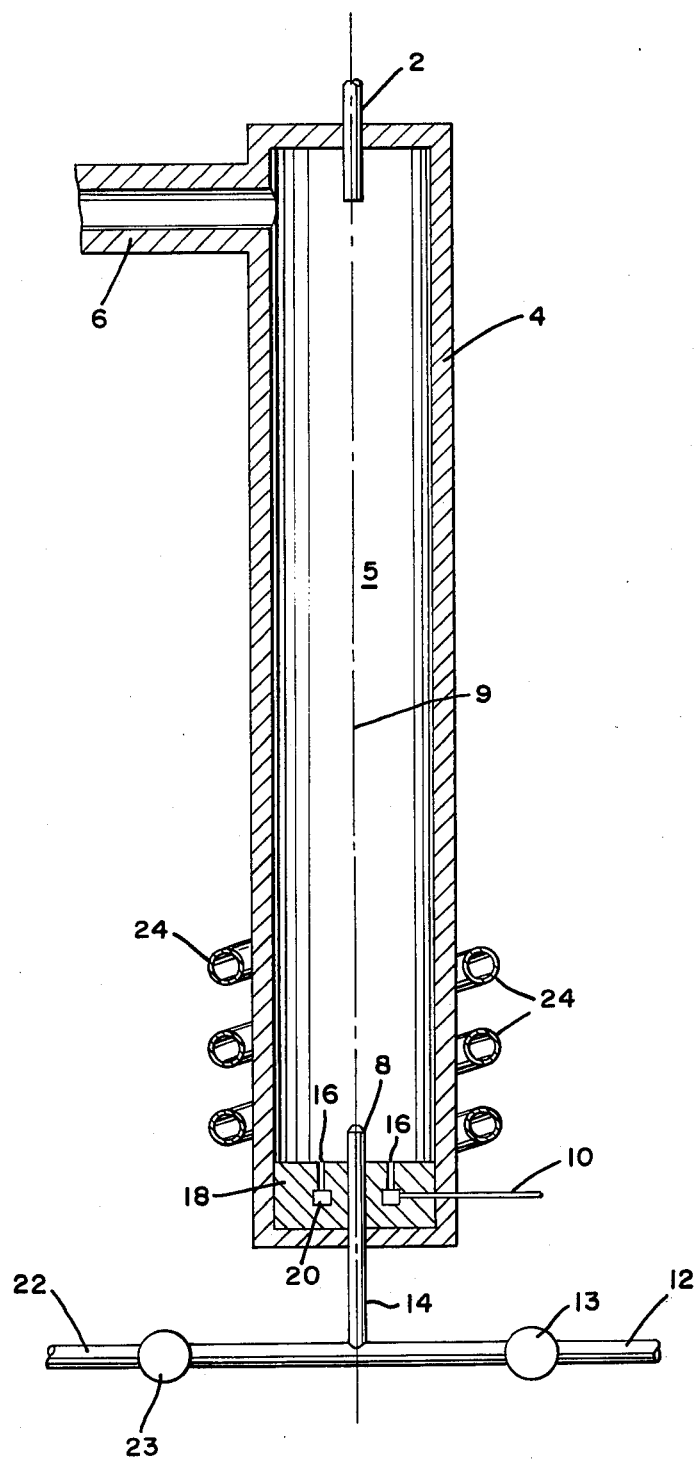

The apparatus of the present invention, herein referred to as an axial jet reactor, may be used as a single unit, as is illustrated in the accompanying drawing. Alternatively, one or more serially arranged units, or a plurality of unit reactors arranged for parallel operation, may be employed. Optionally, heat transfer means can be associated with the axial jet reactor to provide cooling of the exit gases which are exited from the reactor.

In use, a gas mixture containing chlorine and oxygen, preferably as molecular chlorine and molecular oxygen, is introduced by a gas jet into an elongated reaction zone, internally disposed within the axial jet reactor, wherein the gas contacts a gas containing ethane, which is introduced, co-current to the flow of the $O_2/Cl_2$ gas mixture, into the annulus surrounding the jet inlet, for formation of ethylene. The ethylene reaction product is removed from the elongated reaction zone through an outlet, which is generally positioned at a point removed from the ethane gas inlet. The reactor of this invention is specifically designed for adiabatic reaction temperatures and, therefore, the design is such that the reaction takes place in the annulus where temperature control to assure adiabatic conditions is possible. In addition to temperature control, the system, of which this reactor is a part, is also designed for careful control of such variables as flow rates, the proportion of reactants, residence time, and importantly, the degree of mixing in the annulus.

Reference is now made to the accompanying drawing which illustrates one embodiment of an axial jet reactor of the present invention.

The axial jet reactor illustrated in the accompanying drawing comprises outer gas-impervous casing, 4 defining inner elongated reaction zone 5; first gas inlet means 14 for introducing gas mixture containing chlorine and oxygen to reaction zone 5, second gas inlet means 10 for introducing gas containing ethane to zone 5, outlet means 6 for withdrawing product gases from the reactor, and heat exchange means for controlling the temperature within zone 5 comprising heating coils 24, and optionally, quench liquid inlet 2. First gas inlet means 14 in the apparatus herein illustrated includes chlorine gas supply line 22 and oxygen gas supply line 12, each provided with a flow meter 23 and 13, respectively, for supplying oxygen and chlorine to gas inlet 14 for subsequent injection into the gas reactor via jet 8.

It will be understood that elongated reaction zone 5 may be symmetrical or assymmetrical in cross-section, although a symmetrical, e.g., a cylindrical, reaction zone is most preferred.

In operation, metered quantities of chlorine and oxygen are introduced to elongated reaction zone 5 via jet 8 after being supplied to gas inlet 14 by means of chlorine gas supply line 22 and oxygen supply lines 12. Ethane-containing gas is introduced to elongated reaction zone 5 by means of gas inlet 10 which communicates a supply source of ethane-containing gas (not shown) with, in the preferred embodiment, gallery 20 comprising a passage surrounding jet 8 and housed within casing 18 at the base of outer casing 4. Gallery 20 communicates with longitudinal reaction zone 5 by means of one or more inlet ports 16. In the preferred operation, the ethane-containing gas is introduced evenly about gas jet 8. Thus, inlet ports 16 preferably comprise a series of separate inlet passageways communicating zone 5 with gallery 20, and are evenly spaced about a chosen circumference whose center substantially corresponds with longitudinal axis 9 of zone 5, for introduction of the gas containing ethane into longitudinal reaction zone 5 evenly about axial gas jet 8. Alternate embodiments of inlets 16 and galley 20 may be easily envisioned by the skilled practioner to effect the introduction of the ethane-containing gas into reaction zone 5.

The axial jet reaction of the present invention may be optionally heated as by means of external heating coils 24. The axial jet reactor should be constructed of materials resistant to chlorine and HCl gas and the organic and chlorinated organic substances which may be produced as by-products in the present invention.

Within the reactor, ethane is subjected to autothermic cracking in the presence of specified amounts of oxygen and chlorine, and under specified conditions of time and temperature. Cracking, which does not require the continuous input of large quantities of heat, is referred to herein as "autothermic" cracking. In conventional cracking of ethane to ethylene a large amount of heat must be supplied by the cracking equipment; on the other hand, in autothermic cracking, the large negative heat of formation of hydrogen chloride and water tends to balance the positive heat of formation of ethylene. Autothermic cracking therefore minimizes heat input requirements, capital investments, recycling and by-product and carbon formation. High conversions of ethane ranging from 20 to 98 percent with concomitant production of ethylene and yield, based on converted ethane, ranging from 100 to 70 percent can be obtained without the need for added catalytic agents.

In carrying out another preferred embodiment of the invention, chlorine, oxygen (or air) and ethane may be preheated by means of heat exchangers to a temperature preferably between 200° and 500° C. before passage into the reaction zone in the axial jet reactor. It is preferably to avoid temperatures above 500° C. for ethane so as to prevent thermal cracking and to avoid temperatures above 300° C. for chlorine so as to protect the equipment against corrosion, since at elevated temperatures, chlorine becomes highly corrosive.

The reactants are maintained in the longitudinal reaction zone within the jet reactor for at least about 0.1 second, and preferably between 0.25 to 2.5 seconds, or for a time sufficient to convert concomitantly from about 20 to 95 percent of the ethane to 96 to 74 percent of ethylene, respectively based on the converted ethane. Temperatures of from about 500° to 1,100° c may be employed in the reaction zone, with temperatures of from about 700° C to below about 1,000° C being preferred, and from about 850° to 950° C being most preferred.

The conversion and yields obtained are greater at temperatures ranging from about 700° to below 1,000° C. and retention times of from about 0.1 to 10 seconds than when the autothermic cracking step is carried out at temperatures in excess of 1,000° C. with retention times of less than 0.1 second. The percent conversion of ethane and the percent ethylene yield based on the ethane converted, bear approximately an inverse relationship.

The pressure employed in reaction zone 5 is not critical to the present invention. Thus, while pressures of from substantially atmospheric up to about 20 psig have been found quite satisfactory, pressures outside this range can also be employed.

The molar ratio of chlorine to ethane in the reaction zone ranges preferably between about 0.1 and 2:1, more preferably from about 0.2 to about 1.2:1, and most probably from about 0.4 to about 0.6:1. The chlorine to ethane molar ratio may vary within the above range as desired to provide the excess of hydrogen chloride and unreacted ethane present in the product stream.

The molar ratio of oxygen to ethane in the reaction zone is in the range of from about 0.001 to 0.5:1, preferably from about 0.005 to 0.5:1, and most preferably from about 0.1 to 0.4:1. The lower ratios improve the ethylene yield by reducing carbon monoxide and methane formation, but also decrease the rate of reaction. The use of these lower ratios requires that the reactants be preheated to a higher temperature. The residence time in the reactor itself is so short that little heat can be transferred there. However, the heat of reaction has been found to raise the reactants to the desired reaction temperature. If the oxygen-to-ethane ratio is adjusted downward to give a near zero heat of reaction, then the reaction preheat temperatures are preferably such that the desired reaction temperature is attained before introduction of the reactants into the reactor. In general, this is not very practical, so that the oxygen to ethane ratio is preferably kept high enough to give a significant temperature rise due to the heat of reaction. This temperature rise is increased by using substantially pure oxygen rather than air, so that required preheat temperatures are then reduced.

To provide the excellent yields and low carbon formation in accordance with the present invention, it is preferred that the flow rates of the gas mixture containing oxygen and chlorine and gas containing oxygen and chlorine and gas containing ethane into the reaction zone be selected such that the stream of the gas mixture containing oxygen and chlorine, which expands generally conically following its introduction into the reaction zone via the axial jet, does not come into contact with the inside walls of the reactor which define the reaction zone, for at least about the first 70 percent of the length of the reactor.

This has been found desirable to prevent formation of substantial turbulence in the reaction zone which would disrupt the surface of discontinuity in the direction of flow adjacent to the axial jet. It is our belief, which should not be held to be limiting, that it is this surface of discontinuity across which oxygen and chlorine migrate into the surrounding space containing the ethane gas for reaction of these substances to form the desired ethylene, which then passes out of the reactor in excellent yield without substantial formation of such yield-depressing by-products an acetylene, methane, carbon monoxide, etc. Increased turbulence would tend to provide conditions approaching a back-mix reactor in which the ethylene product would, due to enhanced residence time in the reactor, be further reacted in greater amounts to form the above undesired by-products.

In addition to ethylene and hydrogen chloride products, various by-products of the autothermic cracking reaction are formed in minor quantities, including water, acetylene, methane, hydrogen and carbon monoxide in addition to elemental carbon. The by-products which account for the greatest reduction in yield are methane and carbon monoxide.

Thereafter, products of the reaction may be quenched, as by introducing a suitable quench liquid directly into the reaction zone, after reaction is completed, to cool the exiting gases preferably to a reaction product temperature below about 600° C., and more preferably below about 500° C. Suitable quenching liquids include water, ethylene dichloride, and any other liquid which does not substantially react with the ethylene product. Water is the preferred quenching liquid. Alternative to, or in addition to the use of direct quenching, cooling coils and/or a cooling jacket may be placed about the gas outlet end of the apparatus. Rapid quenching has been found to aid in suppressing carbon formation and preventing reactor plugging.

To further aid in suppressing carbon formation, steam may be introduced in conventional amounts into the reactor zone either with the gas feed containing the ethane, or with the gas mixture containing oxygen and chlorine, or both.

The ethylene produced in the apparatus in accordance with the present invention may be recovered from the gases which exit the reactor by conventional means, and a discussion of ethylene recovery therefrom is not necessary here.

To remove any carbon which may have formed on reactor walls and exit gas lines periodic decoking of the reactor may be necessary. In performing decoking, the flows of ethane and chlorine into the reactor are stopped, and an oxygencontaining gas, conveniently air, is allowed to pass through the reactor at elevated temperature, e.g., from about 900° to 1000° C. to oxidize the carbon deposits and to form gaseous oxidation products which are carried out of the reactor. The progress of the decoking process may conveniently followed by gas chromatographic analysis of exit gases for carbon monoxide and carbon dioxide.

The process of the present invention may be further illustrated by reference to the following examples.

EXAMPLES 1-10

The reactor used in Examples 1-10 was an axial jet reactor fabricated from 2.5 ID nickel tubing (47.5 inches long), having an inner length-to-diameter ratio of 18.9.

At the base of the reactor was a graphite block having a ¼ inch deep by ½ inch high gallery with 1/16 inch holes drilled into it so that ethane could be introduced evenly about an axial jet in the reactor base. The jet comprised a 1 inch long piece of ¼ inch nickel tubing and was positioned concentrically to the longitudinal axis.

The top of the reactor was fitted with a piece of nickel tube through which water was introduced as a quench liquid. The reactor exit stream passed into the top of a primary cooler which consisted of a jacketed 1-inch ID nickel pipe. The gas phase from the bottom of the primary cooler was passed upward through a packed 2-inch ID nickel column counter-current to cold quench liquid (water at 15° C). The gas stream then passed through a pressure control value to a gas sampling system and then through a rotometer into a packed scrubber before venting. The three reactants, air, $Cl_2$ and $C_2H_6$, are fed through rotometers to their respective preheaters. The chlorine and air are then mixed and fed to the reactor via the axial jet, with the ethane being fed to the gallery surrounding the jet for substantially uniform passage of ethane into the reaction zone about the jet.

The ethane feed rate in all Examples was 0.832 gm moles/min and the chlorine to ethane mole ratio in all Examples was 0.5. The air to ethane mole ratio in Examples 1-4 and 6-10 was 0.5, and in Example 5 this ratio was 0.4. Except in Examples 6 and 9, the upper 50 percent of the reactor exterior was cooled by means of a water cooling jacket, employing water at a temperature of about 30° C. To decrease carbon deposits, steam (about 220° C) was introduced into the reactor with the air feed at a steam rate corresponding to about 17 mole percent of the total air, $Cl_2$ and ethane feeds to the reactor. Reaction zone temperatures in these examples was from about 900° to 1,000° C.

After each run during which ethane, $Cl_2$ and air were passed to the reactor for formation of ethylene, the ethane and chlorine feeds were discontinued and the reactor was decoked at the above temperatures with air as feed. After ethylene formation runs in Examples 1-5, the apparatus was decoked in each Example for a period of about 10 hours. A 2 hour decoking period was employed after the autothermic cracking runs in Examples 6-10. Inspection of the inside of the reactor after decoking showed these walls were clean with no carbon deposits.

Samples of the reactor effluent gas were taken after passing through the primary cooler and the packed scrubbing tower. Samples were taken at half-hour intervals in Examples 1-5 and every 2 hours in Examples 6-10; they were analyzed by gas chromatography, yielding the data set forth in the Table below.

Table

Examples 1 – 10

| Example No.* | Temp. (° C.) | Time of Run (Hrs.) | % C₂H₄ Yield Per pass | C₂H₄ Yield | C₂H₆ Conver. | Sample Gas Composition (Mol % Relative to C₂H₄) | | | | | | | | | |
|---|---|---|---|---|---|---|---|---|---|---|---|---|---|---|---|
| | | | | | | CH₄ | CO | C₂H₆ | CO₂ | C₂H₂ | Combined Unknowns | O₂ | N₂ | C₂H₄Cl₂ | C₂H₃Cl |
| 1 | 1030 | 6 | 68.2 | 76.6 | 89.0 | 19.7 | 31.4 | 16.1 | 4.2 | 2.8 | 10.5 | 24.0 | 182.9 | 3.1 | 1.7 |
| 2 | 1035 | 4 | 55.6 | 57.4 | 96.9 | 75.2 | 56.2 | 5.6 | 3.4 | 6.7 | 11.6 | 15.2 | 228.8 | 8.4 | 0.2 |
| 3 | 955 | 10 | 70.6 | 75.9 | 93.1 | 22.3 | 36.1 | 9.8 | 1.4 | 1.9 | 11.0 | 9.8 | 137.2 | 2.4 | 1.4 |
| 4 | 1070 | 10.5 | 66.2 | 70.8 | 93.5 | 30.3 | 38.6 | 9.7 | 1.5 | 6.0 | 10.7 | 12.1 | 175.3 | 4.3 | 0.1 |
| 5 | 1035 | 6 | 72.7 | 80.9 | 89.9 | 24.4 | 17.2 | 13.9 | 1.3 | 2.2 | 10.4 | 9.7 | 82.3 | 3.7 | 1.0 |
| 6 | 1000 | 5 | 66.0 | 71.1 | 92.8 | 37.4 | 41.3 | 10.9 | 1.4 | 0.7 | 12.2 | 8.0 | 151.7 | 4.9 | 0.3 |
| 7 | 960 | 5 | 70.0 | 78.8 | 88.8 | 23.6 | 27.9 | 16.0 | 1.2 | 0.5 | 10.9 | 8.3 | 130.2 | 2.4 | 1.7 |
| 8 | 960 | 10 | 69.0 | 79.7 | 86.6 | 22.4 | 26.0 | 19.4 | 1.0 | 0.8 | 10.9 | 10.5 | 131.5 | 2.2 | 2.1 |
| 9 | 965 | 14 | 67.5 | 79.2 | 85.3 | 21.6 | 29.4 | 21.9 | 1.3 | 0.1 | 10.2 | 2.9 | 116.3 | 2.2 | 1.3 |
| 10 | 960 | 9 | 68.8 | 79.0 | 87.1 | 23.0 | 27.9 | 18.7 | 1.1 | 0.5 | 10.7 | 7.7 | 127.4 | 2.3 | 1.7 |

*In each Example, water was introduced as quenching liquid directly into the top of the reactor at a rate of from 5 to 10 grams of water per minute.

Attention is drawn to the excellent yields of the ethylene product.

Other modes of applying the principle of the invention may be employed instead of those explained, changes being made as regards the method or compounds herein disclosed, provided the steps or compounds stated by any of the following claims, or the equivalent of said stated steps or compounds, be employed.

We claim:

1. A process for the production of ethylene by the oxidative dehydrogenation of ethane which comprises introducing, under pressure via a gas jet a first gas feed stream containing oxygen and chlorine into an elongated reaction zone internally disposed within an elongated housing; introducing a second gas feed stream containing ethane into said reaction zone as an annulus surrounding said first gas feed stream and flowing cocurrently therewith; maintaining said reaction zone under conditions sufficient to effect reaction of oxygen, chlorine and ethane in said zone to form ethylene; and withdrawing the product reaction mixture containing ethylene from said reaction zone.

2. The process according to claim 1 wherein said reaction zone is maintained at a temperature of from about 500° to 1,100° C.

3. The process according to claim 1 wherein the molar ratio of chlorine to ethane in said reaction zone is in the range of from about 0.1 and 2:1.

4. The process according to claim 1 wherein the molar ratio of oxygen to ethylene in said reaction zone is in the range of from about 0.001 to 0.5:1.

5. The process according to claim 1 wherein said reaction zone is characterized by a length-to-diameter ratio of at least about 3:1.

6. The process according to claim 1 wherein the oxygen, chlorine and ethane reactants are maintained within said reaction zone for a period of at least about 0.1 second.

7. The process according to claim 1 wherein said gas mixture containing oxygen and chlorine is introduced to said elongated reaction zone along the longitudinal axis of said reaction zone.

8. The process according to claim 1 wherein said gas containing ethane is heated to a temperature of up to about 500° C., and said gas mixture containing oxygen and chlorine is heated to a temperature of up to about 300° C., prior to the introduction of these gases into the reaction zone.

9. The process according to claim 8 wherein the molar ratio of chlorine to ethane in the reaction zone is from about 0.2 to about 1.2:1; the molar ratio of oxygen to ethane in the reaction zone is from about 0.005 to 0.5:1, the reactants are maintained in the reaction zone for a period of between about 0.25 and 2.5 seconds; and the reaction zone is maintained at a temperature of from about 700° C. to below about 1,000° C.

10. The process according to claim 1 wherein said gas feed stream comprising the gas mixture containing oxygen and chlorine first contacts the inner surface of said elongated housing downstream of the gas jet at a point in said reaction zone which is at least about 70 percent of the length of said zone from said gas jet.

* * * * *